United States Patent
Tong et al.

(10) Patent No.: US 9,546,406 B2
(45) Date of Patent: Jan. 17, 2017

(54) MICROORGANISMS CAPABLE OF FIXING CARBON OXIDES AND PERFORMING FERMENTATION AND THE PREPARATION METHOD AND USE OF THE SAME

(71) Applicant: GREEN CELLULOSITY CORPORATION, Hsinchu (TW)

(72) Inventors: Chiang-Hsiung Tong, Hsinchu (TW); Chang-Chieh Chen, Hsinchu (TW); Chin-Chen Hsu, Hsinchu (TW); Yi-Te Chou, Hsinchu (TW)

(73) Assignee: GREEN CELLULOSITY CORPORATION, Hsinchu (TW)

( * ) Notice: Subject to any disclaimer, the term of this patent is extended or adjusted under 35 U.S.C. 154(b) by 0 days.

(21) Appl. No.: 14/794,304

(22) Filed: Jul. 8, 2015

(65) Prior Publication Data

US 2016/0076111 A1    Mar. 17, 2016

Related U.S. Application Data

(60) Provisional application No. 62/021,858, filed on Jul. 8, 2014.

(51) Int. Cl.

| | |
|---|---|
| *C12N 1/20* | (2006.01) |
| *C12P 7/52* | (2006.01) |
| *C12R 1/145* | (2006.01) |
| *C12N 15/03* | (2006.01) |
| *C12P 7/04* | (2006.01) |
| *C12P 7/06* | (2006.01) |
| *C12P 7/16* | (2006.01) |
| *C12P 7/54* | (2006.01) |
| *C12P 7/56* | (2006.01) |

(52) U.S. Cl.
CPC .............. *C12R 1/145* (2013.01); *C12N 1/20* (2013.01); *C12N 15/03* (2013.01); *C12P 7/04* (2013.01); *C12P 7/065* (2013.01); *C12P 7/16* (2013.01); *C12P 7/52* (2013.01); *C12P 7/54* (2013.01); *C12P 7/56* (2013.01)

(58) Field of Classification Search
None
See application file for complete search history.

(56) References Cited

FOREIGN PATENT DOCUMENTS

WO    2012080421 A1    6/2012

OTHER PUBLICATIONS

Taiwanese Office Action corresponding to Application No. 104121327; Issued: Jul. 27, 2016.
Xiaofeng Gao, Hai Zhao, Guohua Zhang, Kaize He, and Yanling Jin. Genome Shuffling of Clostridium acetobutylicum CICC 8012 for Improved Production of Acetone-Butanol-Ethanol (ABE). Curr Microbiol. (2012) 65:128-132.

*Primary Examiner* — Iqbal H Chowdhury
(74) *Attorney, Agent, or Firm* — Cantor Colburn LLP

(57) ABSTRACT

A microorganism capable of fixing a carbon oxide and performing fermentation and its preparation method and use are provided, wherein the preparation method comprises:
(a) providing a first parental strain which is able to fix a carbon oxide;
(b) providing a second parental strain which is able to perform fermentation;
(c) preparing a first protoplast and a second protoplast from the first parental strain and the second parental strain, respectively;
(d) subjecting the first protoplast and the second protoplast to fuse to provide a fusant; and
(e) incubating and selecting the fusant to obtain a target strain.

Figure 1:
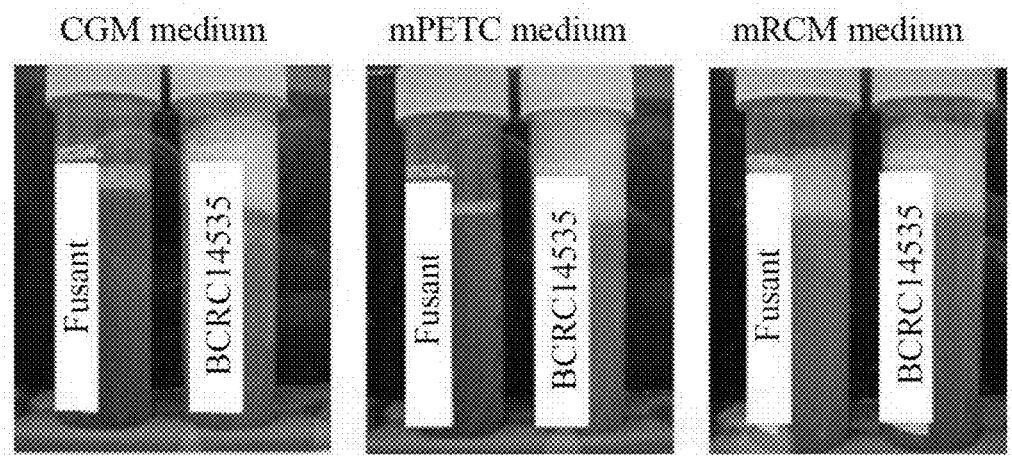

The target strain is useful in the production of an organic compound such as an organic acid and an alcohol, and one embodiment of the target strain is *Clostridium tyrobutyricum* ITRI02001, deposited at German Collection of Microorganisms and Cell Cultures (Deutsche Sammlung von Mikroorganismen and Zellkulturen GmbH, DSMZ) under the accession number DSM 32077.

**9 Cla

MICROORGANISMS CAPABLE OF FIXING CARBON OXIDES AND PERFORMING FERMENTATION AND THE PREPARATION METHOD AND USE OF THE SAME

This application claims the benefit to U.S. Provisional Application No. 62/021,858 filed on Jul. 8, 2014, the subject matter of which is incorporated herein by reference.

BACKGROUND

Technical Field

The present invention relates to a microorganism capable of fixing a carbon oxide and performing fermentation and the preparation method and use of the same, especially relates to the use of the microorganism in the production of an organic compound (e.g., an organic acid, and an alcohol). One embodiment of the microorganism is *Clostridium tyrobutyricum* ITRI02001, deposited at German Collection of Microorganisms and Cell Cultures (Deutsche Sammlung von Mikroorganismen and Zellkulturen GmbH, DSMZ) under the accession number DSM 32077.

Descriptions of the Related Art

As of the early 20th century, microorganisms such as bacteria, yeasts and fungi have been being wildly used in industry to perform fermentation, which converts a biomass material into an organic compound having more economic benefits, such as an organic acid, or an alcohol. Among such microorganism fermentations for the production of an organic compound, the acetone-butanol-ethanol (ABE) pathway is used most wildly. In the ABE pathway of microorganisms, saccharide-containing material (e.g., corns, potatoes, syrups, etc.) can be converted into pyruvate, and the pyruvate can be further converted into acetyl-CoA to produce an organic compound having more economic benefits, such as butyric acid, butanol, and ethanol.

However, the aforementioned process of converting the pyruvate into acetyl-CoA will be accompanied with the release of a carbon oxide (e.g., carbon dioxide) and such release leads to unnecessary carbon loss. It has been known that, if a wild type strain in nature is used in the ABE fermentation process, the conversion from feedstock to product has a highest carbon conversion rate of only about 67%, which leads to a poor yield of organic compound and makes unnecessary cost and resource waste. Therefore, how to increase the carbon conversion rate of the conversion from feedstock to product is a task in this field desired to be solved. One way of solving this task is to further conduct the strain breeding and improvement of the microorganisms to be used in the fermentation process to break the limitation of the heredity characteristics of the microorganisms, and to rebuild the metabolic pathway, inhibit the metabolic shunt or enhance the metabolic flux of the synthetic direction toward the main product, thus to increase the carbon conversion rate of the conversion from feedstock to product.

The present invention is the result of research and development for the above demand. The inventor of the present invention accomplished a method for preparing a microorganism capable of fixing a carbon oxide and performing fermentation. In addition to performing fermentation to produce an organic compound, the microorganism obtained from the method can fix the carbon oxide releasing from the fermentation, recapture the carbon oxide into the fermentation process again. Therefore, the carbon resource would be used more effectively and the unnecessary carbon loss would be reduced, even the requirement of approximately zero carbon loss could be reached.

SUMMARY

An objective of the present invention is to provide a method for preparing a microorganism capable of fixing a carbon oxide and performing fermentation, comprising:
(a) providing a first parental strain which is able to fix a carbon oxide;
(b) providing a second parental strain which is able to perform fermentation;
(c) preparing a first protoplast and a second protoplast from the first parental strain and the second parental strain, respectively;
(d) subjecting the first protoplast and the second protoplast to fuse to provide a fusant; and
(e) incubating and selecting the fusant to obtain a target strain.

Another objective of the present invention is to provide a target strain obtained by the above method.

Yet another objective of the present invention is to provide a method using the above target strain to produce an organic compound, comprising mixing the target strain with a saccharide-containing substrate under an anaerobic atmosphere to perform fermentation. Preferably, the method further comprises using a co-substrate in the fermentation.

Yet another objective of the present invention is to provide a *Clostridium tyrobutyricum* ITRI02001, deposited at German Collection of Microorganisms and Cell Cultures (Deutsche Sammlung von Mikroorganismen and Zellkulturen GmbH, DSMZ) under the accession number DSM 32077.

Yet another objective of the present invention is to provide a method for preparing the above *Clostridium tyrobutyricum* ITRI02001, comprising:
(a) providing a first parental strain, wherein the first parental strain is *Clostridium ljungdahlii* and is able to fix a carbon oxide;
(b) providing a second parental strain, wherein the second parental strain is *Clostridium tyrobutyricum* and is able to perform fermentation;
(c) preparing a first protoplast and a second protoplast from the first parental strain and the second parental strain, respectively;
(d) subjecting the first protoplast and the second protoplast to fuse to provide a fusant; and
(e) incubating and selecting the fusant to obtain the *Clostridium tyrobutyricum* ITRI02001, deposited at German Collection of Microorganisms and Cell Cultures (Deutsche Sammlung von Mikroorganismen and Zellkulturen GmbH, DSMZ) under the accession number DSM 32077.

Yet another objective of the present invention is to provide a method of using the above *Clostridium tyrobutyricum* ITRI02001 to produce an organic compound, comprising mixing the *Clostridium tyrobutyricum* ITRI02001 with a saccharide-containing substrate under an anaerobic atmosphere to perform fermentation. Preferably, the method further comprises using a co-substrate in the fermentation.

The detailed technology and preferred embodiments implemented for the present invention are described in the following paragraphs accompanying the appended drawings for people skilled in this field to well appreciate the features of the claimed invention.

Figure 2A:
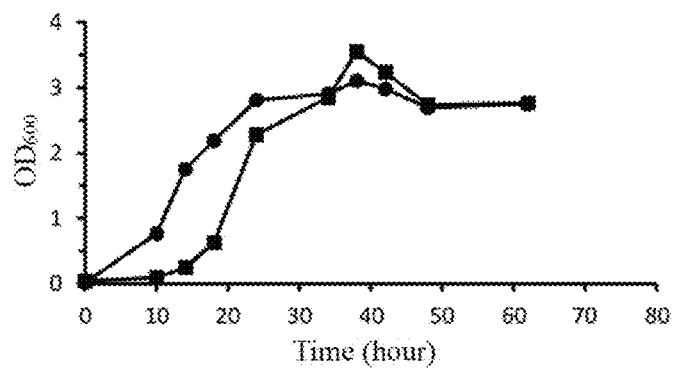
Figure 2B:
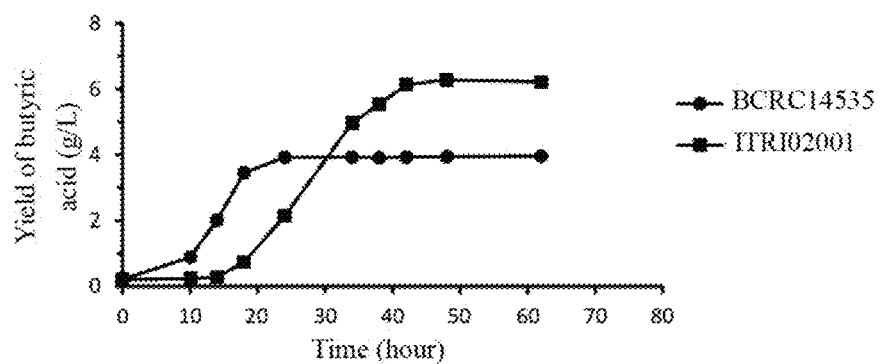
Figure 3:
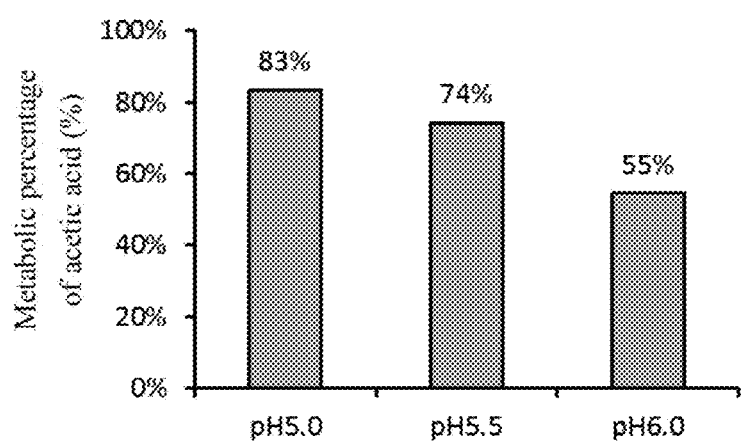

BRIEF DESCRIPTION OF THE DRAWINGS

FIG. 1 is an illustration of the gas-producing situations of the *Clostridium tyrobutyricum* BCRC14535 and a microorganism according to the present invention, both were incubated in three different types of medium (CGM medium, mPETC medium, and mRCM medium), respectively;

FIG. 2A is a curve diagram showing the $OD_{600}$ value of the mRCM medium (containing 10 g/L glucose) at different time points, wherein the *Clostridium tyrobutyricum* BCRC14535 and the *Clostridium tyrobutyricum* ITRI02001 of the present invention were incubated under an anaerobic atmosphere;

FIG. 2B is a curve diagram showing the yield of butyric acid in mRCM medium (containing 10 g/L glucose) at different time points, wherein the *Clostridium tyrobutyricum* BCRC14535 and the *Clostridium tyrobutyricum* ITRI02001 of the present invention were incubated under an anaerobic atmosphere to perform fermentation; and FIG. 3 is a bar diagram showing the metabolic percentage of acetic acid of the *Clostridium tyrobutyricum* ITRI02001 of the present invention incubated in different acidic environments (i.e., pH 5.0, pH 5.5, and pH 6.0).

DESCRIPTION OF THE PREFERRED EMBODIMENT

The following will describe some embodiments of the present invention in detail. However, without departing from the spirit of the present invention, the present invention may be embodied in various embodiments and should not be limited to the embodiments described in the specification. In addition, unless otherwise indicated herein, the expressions "a," "an", "the", or the like recited in the specification of the present invention (especially in the claims) are intended to include the singular and plural forms. Furthermore, the terms "about", "approximate" or "almost" used in the specification substantially represented within ±20% of the stated value, preferably within ±10%, and more preferably within ±5%. The term "microorganism" refers to organisms that is invisible to naked eyes (e.g., bacteria and fungi), which includes the wild types present in nature and mutant types induced by any factors (e.g., natural factor or artificial factor). The term "carbon oxide" refers to carbon monooxide, carbon dioxide, or a combination thereof. Furthermore, unless restricted definitely, the term "saccharide" or "organic compound" recited in the specification include all its isomer forms. Examples of the isomers include, but are not limited to, enantiomers, diastereomers, and conformational isomers.

In the specification, the term "carbon conversion rate" refers to a ratio between the total carbon number of the produced organic compound and the total carbon number of the consumed carbon source in the fermentation, which is calculated by the following Formula 1:

$$\text{carbon conversion rate} = \frac{\text{the total carbon number of produced organic compound}}{\text{the total carbon number of consumed carbon source}} \times 100\% \quad \text{Formula I}$$

The present invention provides a method for preparing a microorganism capable of fixing a carbon oxide and performing fermentation, comprising:

(a) providing a first parental strain which is able to fix a carbon oxide;

(b) providing a second parental strain which is able to perform fermentation;

(c) preparing a first protoplast and a second protoplast from the first parental strain and the second parental strain, respectively;

(d) subjecting the first protoplast and the second protoplast to fuse to provide a fusant; and (e) incubating and selecting the fusant to obtain a target strain.

According to the method of the present invention, any microorganism which is able to fix a carbon oxide can be used as the first parental strain in the step (a). The expression "fix a carbon oxide" refers to a process of converting the carbon oxide into an organic compound by a biochemical reaction. For example, it has been known that there are many microorganisms in nature which can fix the carbon oxide present in their living environment through the Wood-Ljungdahl (WL) pathway, and convert the carbon oxide into acetyl-CoA.

Examples of the strain which are able to fix a carbon oxide through the Wood-Ljungdahl (WL) pathway include, but are not limited to, *Clostridium ljungdahlii, Clostridium autoethanogenum, Clostridium carboxidivorans, Clostridium difficile, Clostridium aceticum, Moorella thermoacetica* (previously known as *Clostridium thermoaceticum*), *Methanobacterium thermoautotrophicum, Desulfobacterium autotrophicum, Clostridium sticklandii, Clostridium thermoautotrophicum, Clostridium formicoaceticum, Clostridium magnum, Acetobacterium carbinolicum, Acetobacterium kivui, Acetobacterium woodii, Acetitomaculum ruminis, Acetoanaerobium noterae*, and *Acetobacterium bakii*.

The above strain which can fix a carbon oxide through the Wood-Ljungdahl (WL) pathway can be used as the first parental strain in the step (a) of the method of the present invention. In one embodiment of the present invention, the first parental strain used in the step (a) is *Clostridium ljungdahlii*.

According to the method of the present invention, any microorganism which is able to perform fermentation can be used as the second parental strain used in the step (b). The term "fermentation" refers to a process for metabolizing a substrate by a microorganism. For example, the strains which are suitable for being the second parental strain in the step (b) of the method of the present invention include, but are not limited to, *Clostridium* sp., *Anaerostipes butyraticus, Anaerostipes caccae, Anaerostipes* sp., *Butyrivibrio crossotus, Butyrivibrio fibrisolvens, Butyrivibrio hungatei, Butyrivibrio proteoclasticus, Clostridiales* sp., *Coprococcus* ART55/1, *Coprococcus catus, Coprococcus comes, Coprococcus eutactus, Eubacterium biforme, Eubacterium cellulosolvens, Eubacterium dolichum, Eubacterium hadrum, Eubacterium hallii, Eubacterium* L2-7, *Eubacterium limosum, Eubacterium oxidoreducens, Eubacterium ramulus, Eubacterium rectale, Eubacterium saburreum, Eubacterium* A2-194, *Eubacterium ventriosum, Lachnospiraceae bacterium, Lachnospiraceae* sp., *Moryella indoligenes, Parasporobacterium paucivorans, Pseudobutyrivibrio ruminis, Pseudobutyrivibrio xylanivorans, Roseburia cecicola, Roseburia faecis, Roseburia hominis, Roseburia intestinalis, Roseburia inulinivorans, Sporobacterium olearium, Anerococcus Octavius, Peptoniphilus asaccharolyticus, Peptoniphilus, duerdenii, Peptoniphilus harei, Peptoniphilus lacrimalis, Peptoniphilus indolicus, Peptoniphilus ivorii, Peptoniphilus* sp., *Sedimentibacter hydroxybenzoicus, Anaerovorax odorimutans, Filifactor alocis, Eubacterium barkeri, Eubacterium infirmum, Eubacterium minutum, Eubacterium nodatum, Eubacterium sulci, Eubacterium moniliforme, llyobacter delafieldii, Oxobacter pfenningii,*

Sarcina maxima, Thermobrachium celere, Butyricicoccus pullicaecorum, Eubacterium A2-207, Gemmiger formicilis, Anaerobaculum mobile, Pelospora glutarica, Thermoanaerobacter yonseiensis, Eubacterium cylindroides, Eubacterium saphenum, Eubacterium tortuosum, Eubacterium yurii margaretiae, Peptococcus anaerobius, Peptococcus niger, Sporotomaculum hydroxybenzoicum, Acidaminococcus intestine, Acidaminococcus fermentans, Acidaminococcus sp., Megasphaera elsdenii, Megasphaera genomosp, Megasphaera micronuciformis, Halanaerobium saccharolyticum, Brachyspira intermedia, Brachyspira alvinipulli, Shuttleworthia satelles, Anaerococcus hydrogenalis Anaerococcus lactolyticus, Anaerococcus prevotii, Anaerococcus tetradius, Anaerococcus vaginalis, Alkaliphilus metalliredigens, Alkaliphilus oremlandii, Anaerofustis stercorihominis, Pseudoramibacter alactolyticus, Anaerotruncus colihominis, Faecalibacterium cf. prausnitzii, Faecalibacterium prausnitzii, Ruminococcaceae bacterium, Subdoligranulum variabile, Thermoanaerobacterium thermosaccharolyticum, Carboxydibrachium pacificum, Carboxydothermus hydrogenoformans, Thermoanaerobacter tengcongensis, Thermoanaerobacter wiegelii, Erysipelotrichaceae bacterium, Carnobacterium sp., Desmospora sp., Acetonema longum, Thermosinus carboxydivorans, Natranaerobius thermophiles, Halanaerobium praevalens, Symbiobacterium thermophilum, Stackebrandtia nassauensis, Intrasporangium calvum, Janibacter sp., Micromonospora aurantiaca, Micromonospora sp., Salinispora arenicola, Salinispora tropica, Verrucosispora maxis, Kribbella flavida, Nocardioidaceae bacterium, Nocardioides sp. Thermomonospora curvata, Haloplasma contractile, Desulfurispirillum indicum, Deferribacter desulfuricans, Rhodoferax ferrireducens, and Stigmatella aurantiaca.

Preferably, the second parental strain used in the step (b) is a strain which is able to perform fermentation through the acetone-butanol-ethanol (ABE) pathway. Examples of the strain which is able to perform fermentation through the ABE pathway include, but are not limited to, Clostridium tyrobutyricum, Clostridium butyricum, Clostridium thermobutyricum, Clostridium cellulovorans, Clostridium polysaccharolyticum, Clostridium populeti, Clostridium aminobutyricum, Clostridium sporosphaeroides, Clostridium innocuum, and Clostridium kluyveri. In one embodiment of the present invention, the second parental strain used in the step (b) is Clostridium tyrobutyricum.

Then, in the step (c), a first protoplast and a second protoplast are prepared from the first parental strain and the second parental strain, respectively. Wherein, the first parental strain and the second parental strain are independently incubated in a suitable medium, and then, until the log (logarithmic) growth phase of both the first parental strain and the second parental strain are reached, then the first protoplast and the second protoplast are prepared from the first parental strain and the second parental strain, respectively.

Any suitable medium can be used to cultivate the first parental strain or the second parental strain, as long as the medium corresponds to the strain to be incubated. The components of medium can be modified according to the strain used. In general, the medium contains such as a carbon source (e.g., glucose, succinate, or a combination thereof), a nitrogen source (e.g., yeast extract, peptone, or a combination thereof), a salt (e.g., magnesium salt, nitrogen salt, phosphor salt, sulfosalt, or a combination thereof), and water, etc. For example, when incubating Clostridium ljungdahlii and/or Clostridium tyrobutyricum, the examples of the medium include, but are not limited to, RCM medium (Reinforced Clostridial Medium), mRCM medium (modified Reinforced Clostridial Medium), CGM medium (Clostridial Growth Medium), mCGM medium (modified Clostridial Growth Medium), PETC medium, and mPETC medium.

The first parental strain and the second parental strain can be processed to provide a corresponding protoplast respectively after both of them have entered the log growth phase, but is not limited thereby. A strain "has entered the log growth phase" refers to that the strain has adapted to the environment and there are enough nutrients in the medium for the strain to propagate greatly, so that the number of the strain can increase logarithmically. And the term "protoplast" refers to a cell whose cell wall has been removed through a mechanical method or an enzymatic method. Any suitable method can be used to provide a protoplast of the first parental strain or the second parental strain (relevant descriptions can be seen in, for example, "Genome Shuffling of Clostridium acetobytylicum CICC 8012 for improved production of acetone-butanol-ethanol (ABE). Curr Microbiol. (2012) 65:128-132," which is entirely incorporated hereinto by reference). For example, the methods can be used to remove the cell wall include, but are not limited to, physical methods such as centrifugation, vortexing, ultrasonication, electroporation, and high osmotic pressure, and chemical methods such as enzymatic method.

In some embodiments of the present invention, an enzymatic method is used to remove the cell wall of the first parental strain and the second parental strain to obtain the first protoplast and the second protoplast, wherein, the enzymes that can be used include, but are not limited to, at least one selected from lysozyme, snailase, zymolase, and cellulase. The suitable enzyme concentration, reaction temperature and reaction time for conducting the enzymatic method can be modified according to the type of the first parental strain and the second parental strain used. In general, the higher the enzyme concentration, or the more the reaction time, that the higher preparation rate of protoplast is. However, if the first parental strain and the second parental strain are treated with an enzyme over time, the regeneration rate of the protoplast may be affected.

In some embodiments according to the present invention, lysozyme was used in step (c) to remove the cell wall of the first parental strain and the second parental strain, to provide the corresponding protoplast thereof. Wherein, when Clostridium ljungdahlii is used as the first parental strain and Clostridium tyrobutyricum is used as the second parental strain, the cell wall of Clostridium ljungdahlii could be removed by treating Clostridium ljungdahlii with 1 mg/ml lysozyme for 15 minutes to 2 hours at 37° C. to obtain the first protoplast, and the cell wall of Clostridium tyrobutyricum could be removed by treating Clostridium tyrobutyricum with 50 µg/ml lysozyme for 15 minutes to 2 hours at 37° C. to obtain the second protoplast.

In the step (d) according to the method of the present invention, the first protoplast and the second protoplast obtained from the step (c) were fused to provide a fusant. The term "fuse" refers to the process of subjecting two protoplasts to break the limitations of the cell membrane so as to combine and become one cell, mix the contents of the two protoplasts, and promote the genome of the two protoplasts to undergo genome shuffling. Any suitable fusion method can be used in the step (d). For example, the fusion method can be a chemical method (e.g., polyethylene glycol (PEG) method), a physical method (e.g., electrofusion method, laser-induced fusion method), or a biological method (e.g., virus-induced fusion method), but is not limited thereto.

Take the chemical method as an example, a polyethylene glycol-containing induction solution can be used to subject the first protoplast and the second protoplast to fuse. Examples of the polyethylene glycol include, but are not limited to, PEG200, PEG 1000, PEG 1450, PEG 1500, PEG 2000, PEG 3000, PEG 3350, PEG 4000, PEG 6000, PEG 8000, and PEG 10000. In one embodiment of the present invention, a SMM solution with high osmotic pressure which contains 30% PEG6000 and 0.05 mol/L $CaCl_2$ was used to subject the first protoplast and the second protoplast to perform an induced-fusion, and the induced-fusion was completed in about 5 to 30 minutes.

After the fusion of the first protoplast and the second protoplast has been completed, the fused protoplast thus obtained is further incubated to provide a fusant. Thereafter, in step (e), the fusant obtained from the step (d) is screened to obtained a target strain.

According to the step (e) of the present invention, to provide a target strain capable of fixing a carbon oxide and performing fermentation, the fusants obtained from the step (d) are incubated in a medium, and the gas-producing situations of the fusants are observed and compared. Furthermore, the fusants are used to conduct fermentation, and then the products of the fermentation are analyzed to calculate and compare the carbon conversion rate of each fusant to convert feedstock into product by performing fermentation. Thereafter, the desired target strain is screened based on the results of the above comparison.

Through the above method of the present invention, a target strain capable of fixing a carbon oxide and performing fermentation can be provided. Therefore, the present invention also provides a target strain obtained from the above method, which has the ability of fixing a carbon oxide of the first parental strain and the ability of performing fermentation of the second parental strain at the same time. For example, when *Clostridium ljungdahlii* is used as the first parental strain of the step (a) and *Clostridium tyrobutyricum* is used as the second parental strain of the step (b) in the above method of the present invention, a *Clostridium tyrobutyricum* ITRI02001 can be obtained. Therefore, the present invention also provides a *Clostridium tyrobutyricum* ITRI02001, deposited at German Collection of Microorganisms and Cell Cultures (Deutsche Sammlung von Mikroorganismen and Zellkulturen GmbH, DSMZ) under the accession number DSM 32077.

Because the target strain provided by the method of the present invention is able to fix a carbon oxide and perform fermentation at the same time, it can use the carbon source in the fermentation system more effectively when performing fermentation. Therefore, the present invention also provides a method of using the target strain to produce an organic compound, wherein, depending on the fermentation ability of the used second parental strain, the target strain obtained therefrom can convert the carbon source such as a saccharide (e.g., a monosaccharide, a disaccharide, an oligosaccharide, a polysaccharide, or a combination thereof) into a different organic compound such as an organic acid, an alcohol, or a combination thereof, but is not limited thereby.

The fermentation is performed by mixing the target strain and a saccharide-containing substrate under an anaerobic atmosphere. The term "anaerobic atmosphere" refers to an atmosphere that contains less than 5 ppm (part per million) of oxygen, preferably less than 0.5 ppm of oxygen, and more preferably less than 0.1 ppm of oxygen. For example, but is not limited to, before the fermentation is performed, an inert gas (e.g., nitrogen, carbon dioxide) can be introduced into the fermentation reactor to purge the reactor, and thus provide the desired anaerobic atmosphere; alternatively, the fermentation is performed in an anaerobic operation box, wherein a palladium catalyst is used to catalyze the reaction of the oxygen in the box and the hydrogen in the anaerobic gas mixture to produce water, and thus provide the desired anaerobic atmosphere.

Generally, in the method of producing an organic compound according to the present invention, any suitable carbon compound can be used as the substrate and mixed with the medium to perform fermentation. For example, a substrate which contains a saccharide (abbreviated to "saccharide-containing substrate") can be provided in the method of the present invention. Examples of the saccharide include, but are not limited to, a monosaccharide (e.g., glucose, fructose, galactose, mannose, arabinose, lyxose, ribose, xylose, ribulose, xylulose, allose, altrose, gulose, idose, talose, psicose, sorbose, tagatose); a disaccharide (e.g., sucrose, maltose, lactose, lactulose, trehalose, cellobiose); an oligosaccharide (e.g., stachyose, maltotriose, maltotetrose, maltopentaose); and a polysaccharide (e.g., starch, cellulose, glycogen, cyclodextrin, arabinoxylans, guar gum, gum arabic, chitin, gum, alginate, pectin, gellan). Alternatively, a substrate which contains an organic acid (e.g., malic acid, citric acid, succinic acid, lactic acid, acetic acid, formic acid, fatty acid, unsaturated fatty acid, amino acid, glutamic acid), a salt of an organic acid, an ester of an organic acid, or other carbon compounds (e.g., carbon dioxide, a carbonate, a low-carbon alcohol, an alkane) can be provided in the method of the present invention. Preferably, the substrate used in the method for producing an organic compound of the present invention contains a monosaccharide. In one embodiment of the present invention, a glucose-containing substrate was used to provide the carbon source needed in the fermentation.

Optionally, the substrate is admixed with a co-substrate to provide additional carbon source to the target strain when performing fermentation, further increasing the yield of the organic compound. The co-substrate can be any suitable carbon compound, as long as it has no adverse effect on the target strain or the progression of fermentation. Examples of the carbon compound which can be used as the co-substrate include, but are not limited to, acetic acid, glycerol, syngas, and a combination thereof. In one embodiment of the present invention, the amount of the co-substrate was not more than that of the saccharide in the saccharide-containing substrate. For example, when a saccharide-containing substrate is used and acetate or glycerol is used as the co-substrate, the amount of the co-substrate in the substrate mixture is about 0.1 to 1 part by weight of co-substrate per part by weight of saccharide.

In one embodiment of the present invention, glucose was used as the saccharide in saccharide-containing substrate and acetate was used as the co-substrate to provide a substrate mixture with additional carbon source needed in the fermentation, wherein the glucose and acetate are used at a weight ratio of about 5:2 (glucose:acetate).

When the *Clostridium tyrobutyricum* ITRI02001 provided by the present invention is used to perform fermentation to produce butyric acid, acetic acid can be added into the glucose-containing substrate as an additional carbon source to perform the fermentation under an anaerobic atmosphere. It has been found that, a better metabolic percentage of acetic acid will be reached when the fermentation is performed at a pH value of no more than 7 and preferably about 5.0 to about 7.0, and more preferably under a weakly acidic environment having a pH value of about 5.0 to about 6.5 and most preferably about 5.0 to about 5.5. In one embodiment of the present invention, acetic acid was used as the co-substrate to provide a carbon source additional to glucose, to perform fermentation under an acidic environment having a pH value of about 5.0, and a metabolic percentage of acetic acid of up to about 83% was reached.

In another embodiment of the present invention, syngas is used as the co-substrate to provide the target strain an additional carbon source for performing fermentation. The syngas is a gas mixture containing hydrogen and a carbon oxide (e.g., carbon monooxide, carbon dioxide, or a combination thereof). For example, a gas mixture provided by mixing carbon dioxide and hydrogen at a volume ratio of 1:4 (carbon dioxide:hydrogen) can be used as the co-substrate.

In the method for producing an organic compound of the present invention, there is no particular limitation to the order of mixing the substrate, co-substrate, and target strain. The substrate and/or the co-substrate can be added at one time or in several batches before the fermentation begins or during the process of the fermentation. The target strain can be supplemented optionally. For example, the saccharide-containing substrate, co-substrate, and target strain can be mixed at one time before performing the fermentation; and the saccharide-containing substrate and/or the co-substrate also can be divided into two or more equal or unequal batches, and then added into the reactor before the fermentation begins or during the process of the fermentation.

Depending on the fermentation ability of the second parental strain used, the present invention can provide target strains having different fermentation abilities, which can be used to provide a different organic compound as the product of fermentation. Examples of the organic compound include, but are not limited to, an organic acid, an alcohol, and a combination thereof. Preferably, the organic compound is a C1-C4 organic acid and/or a C1-C4 alcohol; more preferably, the organic compound is at least one of acetic acid, propionic acid, butyric acid, lactic acid, ethanol, isopropanol, and butanol. In one embodiment of the present invention, the organic compound is butyric acid. As illustrated in the following example, with the use of the method for producing an organic compound according to the present invention, the carbon conversion rate can be more than 67%.

The present invention will be further illustrated in details with specific examples as follows. However, the following examples are provided only for illustrating the present invention, and the scope of the present invention is not limited thereby.

EXAMPLES

The components or source of the materials used in the following examples are listed as follows, respectively:
(a) mRCM medium (yeast extract: 3 g/L, meat extract: 10 g/L, peptone: 5 g/L, sodium chloride: 5 g/L, sodium acetate: 5 g/L, L-cysteinium: 0.5 g/L).
(b) SMM solution (sucrose: 0.5 mM, maleic acid: 20 mM, magnesium chloride: 20 mM, pH=6.5).
(c) SMM fusion inducing solution (SMM solution further added with 30% of PEG 6000 and 0.05 M of calcium chloride).
(d) CGM medium (yeast extract: 5 g/L, peptone: 5 g/L, $(NH_4)_2SO_4$: 3 g/L, $K_2HPO_4$: 1.5 g/L, $MgSO_4.7H_2O$: 0.6 g/L, $FeSO_4.7H_2O$: 0.03 g/L, L-cysteinium: 0.5 g/L).
(e) CGM agar plate (CGM medium, further added with D-(+)-glucose (10 g/L) and agar (15 g/L)).
(f) mPETC medium (relevant description can be seen in Taiwan Patent Publication No. 201441366).
(g) Regenerated medium (mRCM medium, further added with D(+)glucose (10 g/L), sucrose (0.5 M), magnesium chloride (25 mM), calcium chloride (25 mM), and L-cysteinium (0.5 g/L)).
(h) Regenerated agar plate (regenerated medium, further added with casein hydrolysate (10 g/L) and agar (15 g/L)).

In the following examples, the air-tight container (e.g., air-tight bottle, centrifuge tube) is prepared by the following operation to provide an anaerobic atmosphere. The air-tight container and the rubber bung were covered with aluminum foil, and then sterilized under high temperature and high pressure (e.g., 121° C., 1.2 atm) to make sure that no microorganisms would interfere therewith. After the sterilization of the air-tight container was completed, the outside residual moisture was removed by placing the container in an oven to prevent microorganism contamination caused by residual moisture during the operation. Thereafter, the dried air-tight container was transferred into an anaerobic operation box through the transfer box appended to the anaerobic operation box. After the sealing aluminum foil was slightly loosened, the palladium catalyst (purchased from Thermo Scientific, Inc., product number: BR0042) appended to the anaerobic operation apparatus was used to deplete the oxygen in the air-tight container, to provide an anaerobic atmosphere (i.e., the concentration of oxygen in the container is less than 0.5 ppm).

Example 1

Preparation of Fusant (1-1) Providing Parental Strains

*Clostridium ljungdahlii* BCRC17797 which is able to fix a carbon oxide and *Clostridium tyrobutyricum* BCRC14535 which is able to perform fermentation were chosen as the parental strains.

(1-2) Preparing Protoplasts mRCM medium were mixed with glucose to provide a medium mixture with a glucose concentration of 10 g/L, and then the medium mixture was deoxygenated. Thereafter, 40 ml of the deoxygenated medium mixture was injected into two deoxygenated centrifuge tubes respectively. Then, the two parental strains chosen in (1-1) were independently inoculated into the medium mixture kept in the centrifuge tubes. The inoculated medium mixtures kept in the centrifuge tubes were incubated in a 37° C. anaerobic box until the $OD_{600}$ (the absorbance at a wavelength of 600 nm) of *Clostridium ljungdahlii* contained therein reached about 0.8, and the $OD_{600}$ of *Clostridium tyrobutyricum* contained therein reached about 1.5 (i.e., the two parental strains had grown into the mid log growth phase). Two strain suspensions obtained therefrom were collected and centrifuged at a speed of 5000 rpm respectively, and two insoluble were obtained respectively therefrom.

The two insoluble were processed by the following operation respectively: washed with 40 ml of SMM solution for twice, and then resuspended with 10 ml of SMM solution.

Then, lysozyme was added into the insoluble-containing SMM solution to lead the final concentration of the lysozyme in the *Clostridium ljungdahlii*-containing SMM solution and the *Clostridium tyrobutyricum*-containing SMM solution to be 1 mg/ml and 50 mg/ml, respectively. The mixtures obtained therefrom were kept under a 37° C.

environment for about 15 minutes to 2 hours. Finally, a microscope was used to observe and make sure that the protoplasts of *Clostridium ljungdahlii* and *Clostridium tyrobutyricum* have been generated.

(1-3) Providing Fusant

The above two protoplasts obtained from (1-2) were mixed in equal volumes under room temperature to provide a protoplast mixture. The protoplast mixture was added with SMM induced-fusion solution at a volume ratio of protoplast mixture:SMM induced-fusion solution=1:10, and kept for about 5 minutes to 30 minutes to induce the two protoplast to fuse, and a fused protoplast was obtain therefrom.

The fused protoplast was washed with SMM solution for twice. Thereafter, the fused protoplast was suspended in a glucose (10 g/L)-containing regenerated medium (this medium was deoxygenated and kept in a deoxygenated centrifuge tube), and rested in a 37° C. anaerobic incubator and incubated for about 3 to 7 hours, and then, centrifuged at a speed of 4500 rpm, and an insoluble was obtained therefrom. The insoluble was resuspended in a regenerated medium, and then the medium obtained therefrom was spread onto a regenerated agar plate. The plate was placed in a 37° C. incubator for about 48 to 72 hours, and different colonies were generated (i.e., fusant was obtained) therefrom.

(1-4) Incubating and Selecting the Target Strain

Different colonies (i.e., fusants) obtained from (1-3) and *Clostridium tyrobutyricum* BCRC14535 were independently inoculated into three types of medium, which were CGM medium containing 10 g/L glucose, mPETC medium containing 10 g/L glucose, and mRCM medium containing 10 g/L glucose (those mediums were deoxygenated and kept in deoxygenated 50 ml centrifuge tubes). The inoculated mediums were incubated in a 37° C. anaerobic incubator until the fusants or *Clostridium tyrobutyricum* BCRC14535 contained therein all grown into the mid log growth phase (i.e., $OD_{600}$ was about 1.5). The gas-producing situation of each fusant and *Clostridium tyrobutyricum* BCRC14535 were observed. Fusant which has a gas production amount significantly lower than that of *Clostridium tyrobutyricum* BCRC14535 (as shown in FIG. 1), was screened out to obtain a target strain.

The target strain was analyzed by a phylogenetic analysis, and the results indicate that the target strain has a 16S rRNA fragment as presented by SEQ ID NO: 1. As compared, there is an identity more than 99% between the SEQ ID NO: 1 and the 16S rRNA fragment of *Clostridium tyrobutyricum* BCRC14535, so that the target strain is confirmed as *Clostridium tyrobutyricum*, and named as ITRI02001. Wherein, the colony formed by incubating the *Clostridium tyrobutyricum* ITRI02001 on a CGM agar plate has a brown-yellow color, a slightly embossed center, and an appearance of irregular edge.

Example 2

Test of the Physiological Properties of *Clostridium tyrobutyricum* ITRI02001 and *Clostridium tyrobutyricum* BCRC14535 mRCM medium were mixed with glucose and to provide a medium mixture with a glucose concentration of 10 g/L, and then the medium mixture was deoxygenated, thereby providing for further use. Two strain suspensions obtained therefrom were collected and centrifuged at a speed of 5000 rpm respectively, and two insoluble were obtained respectively therefrom.

40 ml of the above deoxygenated medium mixture was injected into two 50 ml centrifuge tubes respectively. Then, *Clostridium tyrobutyricum* BCRC14535 and *Clostridium tyrobutyricum* ITRI02001 were independently inoculated into the above medium mixture kept in the centrifuge tubes. The medium mixture kept in the centrifuge tubes were incubated in a 37° C. anaerobic incubator until the stains contained therein had grown into the mid log growth phase (i.e., the $OD_{600}$ of *Clostridium tyrobutyricum* BCRC14535 and *Clostridium tyrobutyricum* ITRI02001 reached about 1.5, respectively). Two strain suspensions obtained therefrom were diluted with mRCM medium at a volume ratio of 1:200 (strain suspension:mRCM medium) in two deoxygenated medium mixture (150 ml)-containing air-tight bottles respectively. The bottles were placed in a 37° C. anaerobic incubator for incubating the strains. During the cultivation, the value of $OD_{600}$ were measured at different time points to analyze the growth situation of *Clostridium tyrobutyricum* BCRC14535 and *Clostridium tyrobutyricum* ITRI02001. At the same time, Agilent 1100 series high performance liquid chromatography (HPLC) and Aminex HPX-87H (300 mm×7.8 mm) column were used to analyze the constituent of organic compound and the amount of glucose contained in the medium obtained from the above processes. The results of analysis are shown in FIGS. 2A and 2B.

As shown in FIG. 2A, under the same cultivation condition, *Clostridium tyrobutyricum* BCRC14535 and *Clostridium tyrobutyricum* ITRI02001 had different growth rates. This result indicates that *Clostridium tyrobutyricum* ITRI02001 which obtained from the fusion of protoplasts is different from its parental *Clostridium tyrobutyricum* BCRC14535.

On the other hand, as shown in FIG. 2B, being incubated under the same cultivation condition for about 35 hours, as compared to *Clostridium tyrobutyricum* BCRC14535, the yield of butyric acid of *Clostridium tyrobutyricum* ITRI02001 was significantly higher. This result indicates that as compared to *Clostridium tyrobutyricum* BCRC14535, under the same incubating condition, *Clostridium tyrobutyricum* ITRI02001 has a better efficiency on producing butyric acid, and this result again suggest that the two aforementioned strains have different physiological properties, are different strains.

Example 3

Test of the Efficiency of *Clostridium tyrobutyricum* ITRI02001 on Producing an Organic Compound (3-1) Comparison of the Carbon Conversion Rate of *Clostridium tyrobutyricum* BCRC14535 and ITRI02001 mRCM medium was mixed with glucose to provide a medium mixture with a glucose concentration of 10 g/L and an acetic acid concentration of 4 g/L, and then the medium mixture was deoxygenated, thereby providing for further use.

40 ml of the above deoxygenated medium mixture was injected into two 50 ml centrifuge tubes respectively. Then, *Clostridium tyrobutyricum* BCRC14535 and *Clostridium tyrobutyricum* ITRI02001 were independently inoculated into the above medium mixture kept in the centrifuge tubes. The inoculated medium mixtures kept in the centrifuge tubes were incubated in a 37° C. anaerobic incubator to subject the strains contained therein to perform fermentation for 48 hours. Thereafter, Agilent 1100 series high performance liquid chromatography and Aminex HPX-87H (300 mm×7.8 mm) column were used to analyze the amount of glucose, acetic acid, and butyric acid contained in the medium obtained from the above processes. The results are shown in Table 1. Besides, the carbon conversion rates were calculated by Formula 2, and the results are also shown in Table 1.

$$\frac{\dfrac{\text{yield of butyric acid}}{\text{molecular wight of butyric acid}} \times 4}{\dfrac{\text{consumption of glucose}}{\text{molecular wight of glucose}} \times 6 + \dfrac{\text{consumption of acetic acid}}{\text{molecular wight of acetic acid}} \times 2} \times 100\% \qquad \text{Formula 2}$$

TABLE 1

|  | Consumption of glucose (g/L) | Consumption of acetic acid (g/L) | Yield of butyric acid (g/L) | Carbon conversion rate of butyric acid (%) |
|---|---|---|---|---|
| *Clostridium tyrobutyricum* BCRC14535 | 9.76 | −0.4 | 4.72 | 67% |
| *Clostridium tyrobutyricum* ITRI02001 | 9.92 | 3.8 | 8.57 | 85% |

As shown in Table 1, being incubated in the medium containing glucose and acetic acid, *Clostridium tyrobutyricum* BCRC14535 did not consume acetic acid, but produced additional acetic acid instead. As calculated by Formula 2, the carbon conversion rate provided by *Clostridium tyrobutyricum* BCRC14535 was only about 67%. On the other hand, under the same cultivation condition, *Clostridium tyrobutyricum* ITRI02001 could use acetic acid as additional carbon source in fermentation to produce more butyric acid. As calculated by Formula 2, the carbon conversion rate provided by *Clostridium tyrobutyricum* ITRI02001 was about 85%. These results indicate that *Clostridium tyrobutyricum* ITRI02001 of the present invention can use acetic acid as co-substrate, to further produce butyric acid in a larger amount, to provide a better carbon conversion rate.

(3-2) Metabolic Percentages of Acetic Acid of *Clostridium tyrobutyricum* ITRI02001 Under Different pH Values.

The steps of example (3-1) were repeated, but the pH value of the used medium mixtures were adjusted to be 5.0, 5.5, and 6.0, respectively, by adding MES buffer (purchased from Sigma-Aldrich: 200 mM) and sodium hydroxide solution before *Clostridium tyrobutyricum* ITRI02001 was incubated therein, to compare the acetic acid metabolic percentage of *Clostridium tyrobutyricum* ITRI02001 under different pH values. The results are shown in FIG. 3.

As shown in FIG. 3, *Clostridium tyrobutyricum* ITRI02001 can provide an excellent metabolic percentage of acetic acid under an environment at a pH value of no higher than 7, and the metabolic percentage was increased along with the reduction of pH value. Wherein, under the cultivation condition at a pH value of 6.0, 5.5, and 5.0, the metabolic percentage of acetic acid was about 55%, about 74%, and about 83%, respectively.

(3-3) Carbon Conversion Rates of *Clostridium tyrobutyricum* ITRI02001 Under Different Gas Atmospheres.

mRCM medium was mixed with glucose to provide a medium mixture with a glucose concentration of 5 g/L and an acetic acid concentration of 4 g/L, and then the medium mixture was deoxygenated, thereby providing for further use.

40 ml of the above deoxygenated medium mixture was injected into two 50 ml air-tight bottles respectively. Then, the *Clostridium tyrobutyricum* BCRC14535 and *Clostridium tyrobutyricum* ITRI02001 were independently inoculated into the above medium mixture kept in the air-tight bottles, at the same time, an additional 20 psi syngas (20% carbon dioxide, 80% hydrogen) was introduced thereinto, to further provide a gas co-substrate (hereinafter referred to as the "syngas introduced" experimental group). Thereafter, the inoculated medium mixtures kept in the air-tight bottles were incubated in a 37° C. anaerobic incubator to subject the strains contained therein to perform fermentation for 48 hours. Agilent 1100 series high performance liquid chromatography and Aminex HPX-87H (300 mm×7.8 mm) column were used to analyze the amount of glucose, acetic acid, and butyric acid contained in the medium obtained from the above processes. Besides, the carbon conversion rates were calculated by Formula 2. The results are all shown in Table 2.

The aforementioned experiment process was repeated, but without any additional gas being introduced into the deoxygenated medium mixture (hereinafter referred to as the "no additional gas introduced" control group). Besides, the aforementioned experiment process was repeated as the same, but an additional 20 psi nitrogen was introduced into the air-tight bottles instead (i.e., the syngas was replaced with nitrogen) (hereinafter referred to as the "nitrogen introduced" reference group). The results of the control group and reference group are also shown in Table 2.

TABLE 2

|  | Consumption of glucose (g/L) | Consumption of acetic acid (g/L) | Yield of butyric acid (g/L) | Carbon conversion rate of butyric acid (%) |
|---|---|---|---|---|
| *Clostridium tyrobutyricum* BCRC14535 (no additional gas introduced) | 4.80 | 0 | 2.21 | 63% |
| *Clostridium tyrobutyricum* BCRC14535 (syngas introduced) | 4.80 | 0 | 2.25 | 64% |
| *Clostridium tyrobutyricum* ITRI02001 (no additional gas introduced) | 4.77 | 1.49 | 4.00 | 87% |
| *Clostridium tyrobutyricum* ITRI02001 (nitrogen introduced) | 4.77 | 1.63 | 4.09 | 87% |

TABLE 2-continued

| | Consumption of glucose (g/L) | Consumption of acetic acid (g/L) | Yield of butyric acid (g/L) | Carbon conversion rate of butyric acid (%) |
|---|---|---|---|---|
| *Clostridium tyrobutyricum* ITRI02001 (syngas introduced) | 4.77 | 2.46 | 4.99 | 94% |

As shown in Table 2, as compared to *Clostridium tyrobutyricum* BCRC14535 of the "no additional gas introduced" control group, the yields and the carbon conversion rates of butyric acid of *Clostridium tyrobutyricum* BCRC14535 of the "syngas introduced" experimental group were not significantly increased. However, as compared to *Clostridium tyrobutyricum* ITRI02001 of the "no additional gas introduced" control group, the yields and the carbon conversion rates of butyric acid of *Clostridium tyrobutyricum* ITRI02001 of the "syngas introduced" experimental group were all have significantly increased. These results indicate that different from *Clostridium tyrobutyricum* BCRC14535, which cannot use syngas to produce butyric acid in fermentation, *Clostridium tyrobutyricum* ITRI02001 of the present invention can use syngas (carbon dioxide and hydrogen) effectively to produce more butyric acid and thus provide a better carbon conversion rate of butyric acid.

On the other hand, as compared to *Clostridium tyrobutyricum* ITRI02001 of the "no additional gas introduced" control group, the yields and the carbon conversion rates of butyric acid of *Clostridium tyrobutyricum* ITRI02001 of the "nitrogen introduced" reference group were not significantly increased. These results confirm that the increment in the yield and the carbon conversion rate of butyric acid of *Clostridium tyrobutyricum* ITRI02001 of the "syngas introduced" experimental group is not purely caused by performing fermentation under a higher gas pressure, but is caused by the gas co-substrate (i.e., syngas) which can provide additional carbon source. These results also confirm that *Clostridium tyrobutyricum* ITRI02001 is able to fix carbon, and thus can include the carbon dioxide of the syngas into fermentation (i.e., fix the carbon dioxides of the syngas) to produce more butyric acid, and thus provide a better carbon conversion rate of butyric acid.

(3-4) Comparison of the Co-Substrate Metabolic Abilities Between *Clostridium tyrobutyricum* BCRC14535 and ITRI02001 mRCM medium was mixed with glucose and glycerol to provide a medium mixture with a glucose concentration of 10 g/L, an acetic acid concentration of 4 g/L, and a glycerol concentration of 3 g/L, and then the medium mixture was deoxygenated, thereby providing for further use.

40 ml of the above deoxygenated medium mixture was injected into two 50 ml centrifuge tubes respectively. Then, *Clostridium tyrobutyricum* BCRC14535 and the *Clostridium tyrobutyricum* ITRI02001 were independently inoculated into the above medium mixture kept in the centrifuge tubes. The inoculated medium mixture kept in the centrifuge tubes were incubated in a 37° C. anaerobic incubator to subject the strains contained therein to perform fermentation for 48 hours. And then, Agilent 1100 series high performance liquid chromatography and Aminex HPX-87H (300 mm×7.8 mm) column were used to analyze the amount of glucose, acetic acid, glycerol, and butyric acid contained in the medium obtained from the above processes. The results are shown in Table 3.

TABLE 3

| | Consumption of glucose (g/L) | Consumption of acetic acid (g/L) | Consumption of glycerol (g/L) | Field of butyric acid (g/L) |
|---|---|---|---|---|
| *Clostridium tyrobutyricum* BCRC14535 | 10.66 | 0.78 | 1.08 | 5.17 |
| *Clostridium tyrobutyricum* ITRI02001 | 10.64 | 3.21 | 3.0 | 7.86 |

As shown in Table 3, under the same cultivation condition, *Clostridium tyrobutyricum* BCRC14535 could only metabolize about 0.78 g/L acetic acid and about 1.08 g/L glycerol, while *Clostridium tyrobutyricum* ITRI02001 of the present invention could metabolize about 3.21 g/L acetic acid and about 3.0 g/L glycerol. These results indicate that, as compared to the parental strain, *Clostridium tyrobutyricum* ITRI02001 of the present invention has a better ability of metabolizing acetic acid and glycerol.

(3-5) Metabolic Ability of *Clostridium tyrobutyricum* ITRI02001

Ingredients shown in Table 4 were used to prepare different medium mixture, and then the medium mixtures were deoxygenated, thereby providing for further use.

40 ml of the above deoxygenated medium was injected into two 50 ml centrifuge tubes respectively. Then, *Clostridium tyrobutyricum* ITRI02001 was independently inoculated into the medium mixtures kept in the centrifuge tubes. The inoculated medium mixture kept in the centrifuge tubes were incubated in a 37° C. anaerobic incubator to subject the strains contained therein to perform fermentation for 72 hours. And then, Agilent 1100 series high performance liquid chromatography and Aminex HPX-87H (300 mm×7.8 mm) column were used to analyze the amount of glucose, acetic acid, and butyric acid in the above medium obtained from the above processes. The results are shown in Table 5.

TABLE 4

| | | Concentration in medium mixture (g/L) | |
|---|---|---|---|
| Group | Ingredients | Glucose | Acetic acid |
| A | mRCM medium, glucose | 10 | 4 |
| B | mRCM medium | — | 4 |
| C | CGM medium, glucose, acetic acid | 10 | 4 |
| D | CGM medium, acetic acid | — | 4 |

TABLE 5

| Group | Consumption of glucose (g/L) | Consumption of acetic acid (g/L) | Field of butyric acid (g/L) |
|---|---|---|---|
| A | 9.88 | 3.40 | 6.24 |
| B | 0 | 0.23 | 0.27 |

TABLE 5-continued

| Group | Consumption of glucose (g/L) | Consumption of acetic acid (g/L) | Field of butyric acid (g/L) |
|---|---|---|---|
| C | 9.89 | 3.36 | 6.17 |
| D | 0 | 0.15 | 0.04 |

As shown in Table 5, no matter mRCM medium or CGM medium was used, under the condition that glucose and acetic acid were contained in the medium at the same time (i.e., A group and C group), *Clostridium tyrobutyricum* ITRI02001 can perform fermentation to convert glucose and acetic acid into butyric acid. However, under the condition that only acetic acid co-substrate was contained in the medium (i.e., B group and D group), the consumptions of acetic acid and the yields of butyric acid were all significantly decreased. These results indicate that under the condition without saccharide carbon source, *Clostridium tyrobutyricum* ITRI02001 cannot use acetic acid co-substrate effectively to perform fermentation to produce butyric acid.

The above experimental results indicate that, *Clostridium tyrobutyricum* ITRI02001 of the present invention can convert the saccharide carbon source by performing fermentation to produce butyric acid in a larger amount, wherein the carbon conversion rate of butyric acid is even more than the theoretical value (i.e., 67%). Without being limited by theory, it is believed that *Clostridium tyrobutyricum* ITRI02001 is able to fix carbon dioxide and further convert the carbon dioxide into butanoid acid, to produce the desired product from material substrates more commercially. Besides, when saccharides are used as the carbon source in fermentation, *Clostridium tyrobutyricum* ITRI02001 of the present invention can further use co-substrate (e.g., acetic acid, glycerol, syngas) to produce more organic compound(s), and thus provides a higher carbon conversion rate.

BRIEF DESCRIPTION OF REFERENCE NUMERALS

Not applicable.

DEPOSIT OF BIOLOGICAL MATERIAL

Depository institute: DSMZ (Deutsche Sammlung von Mikroorganismen and Zellkulturen GmbH)
Address: Inhoffenstraβe 7 B, 38124 Braunschweig, GERMANY
Date: Jun. 26, 2015
Deposited biological material: *Clostridium tyrobutyricum* ITRI02001
Accession number: DSM 32077

What is claimed is:

1. A *Clostridium tyrobutyricum* ITRI02001, deposited at German Collection of Microorganisms and Cell Cultures (Deutsche Sammlung von Mikroorganismen and Zellkulturen GmbH, DSMZ) under the accession number DSM 32077.

2. A method of using the *Clostridium tyrobutyricum* ITRI02001 as claimed in claim 1 to produce an organic compound, comprising mixing the *Clostridium tyrobutyricum* ITRI02001 with a saccharide-containing substrate under an anaerobic atmosphere to perform fermentation.

3. The method as claimed in claim 2, wherein the organic compound is at least one of an organic acid and an alcohol.

4. The method as claimed in claim 2, wherein the organic compound is at least one of acetic acid, propionic acid, butyric acid, lactic acid, ethanol, isopropanol, and butanol.

5. The method as claimed in claim 2, wherein the organic compound is butyric acid.

6. The method as claimed in claim 2, wherein the saccharide-containing substrate is admixed with a co-substrate prior to being mixed with the target strain, and the co-substrate contains at least one of acetic acid, glycerol, and synthesis gas.

7. The method as claimed in claim 6, wherein the saccharide-containing substrate and the co-substrate are used at a weight ratio of saccharide-containing substrate:co-substrate=10:1 to 1:1.

8. The method as claimed in claim 6, wherein the co-substrate contains acetic acid and the fermentation is performed at a pH value of about 5.0 to about 7.0.

9. The method as claimed in claim 2, wherein the fermentation has a carbon conversion rate of more than 67%.

\* \* \* \* \*

SEQUENCE LISTING

<160> NUMBER OF SEQ ID NOS: 1

<210> SEQ ID NO 1
<211> LENGTH: 1056
<212> TYPE: DNA
<213> ORGANISM: Clostridium tyrobutyricum

<400> SEQUENCE: 1
cacatgcaag tcgagcgatg aaaccccttc gggggtggat tagcggcgga cgggtgagta 60
acacgtgggt aacctgcctc aaagtggggg atagccttcc gaaaggaaga ttaataccgc 120
ataaagccaa gtttcacatg gaatttggat gaaaggagta attcgctttg agatggaccc 180
gcggcgcatt agttagttgg tggggtaatg gcctaccaag acagcgatgc gtagccgacc 240
tgagagggtg atcggccaca ttggaactga gatacggtcc agactcctac gggaggcagc 300
agtggggaat attgcacaat gggcgaaagc ctgatgcagc aacgccgcgt gagtgatgaa 360
ggtcttcgga ttgtaaagct ctgtcttttg ggacgataat gacggtacca aaggaggaag 420
ccacggctaa ctacgtgcca gcagccgcgg taatacgtag gtggcgagcg ttgtccggat 480
ttactgggcg taaagggtgc gtaggcggat gtttaagtga gatgtgaaat acccgggctt 540
aacttgggtg ctgcatttca aactggatat ctagagtgca ggagaggaga atggaattcc 600
tagtgtagcg gtgaaatgcg tagagattag gaagaacacc agtggcgaag gcgattctct 660
ggactgtaac tgacgctgag gcacgaaagc gtgggtagca aacaggatta gataccctgg 720
tagtccacgc cgtaaacgat gagtactagg tgtaggaggt atcgacccct tctgtgccgc 780
agtaaacaca ttaagtactc cgcctgggaa gtacgatcgc aagattaaaa ctcaaaggaa 840
ttgacggggg cccgcacaag cagcggagca tgtggtttaa ttcgaagcaa cgcgaagaac 900

-continued

```
cttacctgga cttgacatcc cctgaataac ctagagatag gcgaagccct tcggggcagg    960
gagacaggtg gtgcatggtt gtcgtcagct cgtgtcgtga gatgttaggt taagtcctgc   1020
aacgagcgca acccttattg ttagttgcta acattc                             1056
```